United States Patent [19]

Yanai et al.

[11] Patent Number: 5,371,302
[45] Date of Patent: Dec. 6, 1994

[54] PROCESS FOR PREPARING PRILLED BISPHENOL A

[75] Inventors: Hiroshi Yanai, Kitakyushu; Tadayoshi Matsuo, Naokata; Masanori Nagase, Kitakyushu; Tsohikazu Maruyama, Kitakyushu; Toshihiko Furukawa, Kitakyushu; Katsuhiko Sakura, Kitakyushu; Yoshiaki Matsui, Kitakyushu; Takamasa Minami, Kitakyushu; Nobuo Moriya, Yokohama; Sachio Asaoka, Yokohama; Kouji Sakashita, Yokohama; Nobuyuki Suda, Yokohama; Keiji Shimoda, Yokohama; Susumu Yamamoto, Yokohama; Makoto Nomura, Yokohama, all of Japan

[73] Assignees: Nippon Steel Chemical Co., Ltd.; Chiyoda Corp., Tokyo, Japan

[21] Appl. No.: 45,204

[22] Filed: Apr. 13, 1993

[30] Foreign Application Priority Data

| Apr. 14, 1992 | [JP] | Japan | 4-120044 |
| Apr. 16, 1992 | [JP] | Japan | 4-121068 |
| Sep. 30, 1992 | [JP] | Japan | 4-283479 |
| Sep. 30, 1992 | [JP] | Japan | 4-283485 |

[51] Int. Cl.$^5$ ............... C07C 37/88; C07C 39/16
[52] U.S. Cl. ............... 568/703; 264/13; 568/723; 568/724
[58] Field of Search .......... 568/724, 723, 703; 264/13

[56] References Cited

U.S. PATENT DOCUMENTS

| 3,518,329 | 6/1970 | Hoogendonk | 264/13 |
| 4,160,110 | 7/1979 | Carnahan | 568/703 |
| 4,533,764 | 8/1985 | Chang et al. | 568/724 |
| 4,894,486 | 1/1990 | Neil et al. | 568/703 |
| 5,091,591 | 2/1992 | Cipullo | 568/703 |

FOREIGN PATENT DOCUMENTS

| 29832 | 12/1990 | Japan . |
| 8805345 | 7/1988 | WIPO . |

Primary Examiner—Joseph E. Evans
Attorney, Agent, or Firm—Birch, Stewart, Kolasch & Birch

[57] ABSTRACT

The invention relates to a process for preparing prilled bisphenol A by granulation which comprises adding compounds soluble in molten bisphenol A, not affecting adversely the melt color of bisphenol A to any significant extent, and have a melting point of 60° C. or more to bisphenol A and granulating and also to a process which comprises adding the reaction mother liquor or cyrstallization mother liquor produced in the manufacturing step of bisphenol A to bisphenol A or the adduct of bispheol A and phenol or a mixture of bispheol A and phenol, removing the phenol, and granulating. The processes yield prilled bispheol A which have high strength and resist powdering.

6 Claims, No Drawings

PROCESS FOR PREPARING PRILLED BISPHENOL A

Field of the Invention and Related Art Statement

This invention relates to a process for preparing prilled bisphenol A.

Bisphenol A or 2,2-bis(4-hydroxyphenyl)propane is solid at normal temperature and available in the form of small spherical granules usually called prills, flakes, or crystals. It is needless to say that the granulated bisphenol A is desirably uniform in shape and particle diameter for ease of handling. Prills obtained by solidifying drops are the most desirable from the viewpoint of the uniformity of shape and preferrable to manufacturing.

It is possible to control the particle diameter and particle size distribution of prills by proper selection of the manufacturing conditions. However, prills may break up and generate dust in handling equipment while in transport. The dust not only creates the possibility of explosion but also makes handling more difficult.

Processes for preparing prilled bisphenol A are described, for example, in U.S. Pat. No. 3,518,329 and W088/05345. They control the shape and strength of prills by controlling the solidifying conditions by such means as addition of seed crystals. Even with the application of these processes, however, prills at times lack sufficient strength and break up to generate dust. In particular, a process for preparing prills by solidifying drops of bisphenol A in a stream of gas does not always produce prills of sufficient strength.

OBJECT AND SUMMARY OF THE INVENTION

The present inventors have conducted extensive studies to improve the strength of prilled bispheol A, found that it becomes more difficult to obtain sufficient strength as the purity of bispheol A increases and that specified components present in a very small amount in bisphenol A are related to the strength of prills, and completed this invention.

Accordingly, it is an object of this invention to provide a process for preparing prilled bisphenol A of high strength which is difficult to break and generate dust.

Thus, in granulation of molten bisphenol A, the first mode of the process of this invention relates to a process for preparing prilled bisphenol A which comprises adding one kind or two or more kinds of compounds soluble in molten bisphenol A, not significantly affecting the melt color of bispheol A, and having a melting point of 60° C. or more to bisphenol A and granulating the mixture.

In granulation of molten bispheol A, the second mode of the process of this invention relates to a process for preparing prilled bispheol A which comprises adding the reaction mother liquor or the crystallization mother liquor produced in the manufacturing step of bisphenol A to the molten bisphenol A or the molten adduct of bisphenol A and phenol or a mixture of bisphenol A and phenol, removing the phenol, and granulating.

The first mode of the process of this invention will be described first.

Bisphenol A is prepared by the reaction of acetone with excess phenol in the presence of an acid catalyst such as hydrochloric acid and acidic ion exchange resins. One of the processes for recovering bisphenol A from the reaction mixture is practiced by removing water, acetone and/or the catalyst from the reaction mixture, cooling the remainder to allow the adduct of bispheol A and phenol to crystallize out, separating the crystals from the mother liquor, and removing the phenol to recover bispheol A. The bispheol A is then prilled.

Byproducts form in addition to bisphenol A in the above-mentioned reaction and they are removed in the purification step to increase the purity of bispheol A normally to 99.9% or more. To the bisphenol A thus purified is added one kind or two or more kinds of compounds which are soluble in molten bisphenol A, do not significantly affect the melt color of bisphenol A, and have a melting point of 60° C. or more before granulation.

The compounds to be added need to satisfy the aforesaid properties. Compounds insoluble in molten bisphenol A are not effective for improving the strength, those significantly affecting the melt color of bisphenol A adversely affect the quality of bisphenol A and the derived products, and those having a melting point below 60° C. produce less or no effects for improving the strength of prilled bisphenol A. In consideration of the effects for improving the strength and the effects on product properties such as coloration, the desirable additives are one kind or two or more kinds of compounds selected from the group of aromatic dicarboxylic acid diesters, phenolic compounds having two phenolic hydroxyl groups and their hydrogenation compounds, and phenolic resins. An example of the aromatic dicarboxylic acid diesters is 2,6-naphthalenedicarboxylic acid dimethyl ester and an example of the phenolic compounds having two phenolic hydroxyl groups is 9,9-bis(4-hydroxyphenyl)fluorene excluding bisphenol A. The phenolic resins include phenolic novolak resins. Preferable compounds are phenolic compounds having two phenolic hydroxyl groups and chemically resembling bisphenol A or their hydrogenation compounds. The addition of these compounds is in the range from 100 to 2,000 ppm, preferably from 300 to 1,000 ppm based on bisphenol A, since a larger addition than this value lowers the purity and a smaller addition is not effective for improving the strength.

Bisphenol A containing the specified compounds is molten, reduced to drops, cooled, and solidified to yield prills. Any of atomizing, dropping, and spreading is applicable as a process for forming drops. There is no specification to the presence or absence of seed crystals and to the cooling process. The size of prills is chosen from the range of 500 to 5,000 μm, suitably 800 to 3,000 μm.

The second mode of the process of this invention will be described next.

According to this process, bisphenol A is obtained by the reaction of acetone with excess phenol in the presence of an acid catalyst such as hydrochloric acid and acidic ion exchange resins. One of the methods to recover bispheol A from the reaction mixture is practiced by removing water, acetone and/or the catalyst from the reaction mixture, cooling the remainder to allow the adduct of bispheol A and phenol to crystallize out, separating the crystals from the mother liquor, and removing the phenol to recover bisphenol A.

The crystals thus formed by cooling are generally separated from the mother liquor by filtration, in particular, with the aid of a centrifugal separator. In the practice of this method, it is desirable to wash the crystals with phenol in order to remove the mother liquor adhering to them. The filtrate separated from the reaction mixture and the filtrate of the mother liquor washed off the crystals are referred to as reaction mother liquor in this invention.

The purity of this adduct can be raised, as proposed in Japan Kokai Tokkyo Koho No. Hei 2-9,832 (1990), by adding phenol to the adduct obtained in the first separation to form a solution or a slurry and causing such solution to crystallize by cooling or separating crystals from such slurry without cooling to carry out the second separation. However, bisphenol A obtained by dissolution in phenol followed by recrystallization tends to yield prills of high strength with difficulty. On the other hand, bisphenol A obtained by formation of a slurry followed by separation of crystals tends to yield prills of low purity. It is desirable to apply phenol washing in the second separation. The filtrate or the filtrate after washing obtained in the second separation is referred to as crystallization mother liquor. The crystallization mother liquor is desirable because it contains a small amount of impurities responsible for coloration.

According to this process, the aforesaid reaction mother liquor or crystallization mother liquor is added, prior to granulation, to high-purity bisphenol A or to the high-purity adduct or mixture of bisphenol A and phenol obtained after the two-step crystallization.

There is no specification regarding bisphenol A to be used in this process, but it is desirable that impurities other than phenol have been removed as much as possible. In the case of the adduct, it is desirably used as crystals separated from the mother liquor in the above-mentioned manner. A mixture of bisphenol A and phenol presents no problem.

The reaction mother liquor or the crystallization mother liquor contains primarily phenol together with a small amount of bisphenol A and small amounts to traces of byproducts. According to a study of the present inventors, these byproducts, even in a very small amount, are able to raise the strength of prilled bisphenol A and their addition to bisphenol A does not cause problems such as coloration. The addition of these mother liquors is adequate if it is in the range from 100 to 2,000 ppm in terms of an increment of trace components in bisphenol A. It is desirably in the range from 300 to 1,000 ppm since a larger addition than this lowers the purity and a smaller addition is not fully effective for improving the strength.

As the reaction mother liquor or the crystallization mother liquor contains a large quantity of phenol, the phenol is removed prior to prilling. The removal of phenol can be effected by distillation, evaporation or stripping, recrystallization, and the like and it is adequate to use distillation or a combination of evaporation and stripping. Prilling is carried out by melting bisphenol A from which phenol has been removed, making the melt into drops, and cooling and solidifying the drops. It is optional what process to apply to the formation of drops; for example, any of atomizing, dropping, and spreading can be adopted. The use of seed crystals or the method for cooling is also optional. The size of prills is in the range of 500 to 5,000 μm, suitably from 800 to 3,000 μm.

Either of the aforesaid processes of this invention can produce prilled bisphenol A which has high strength and resists powdering. In particular, the mother liquors used as additives in the second process are the byproducts of bisphenol A and they are readily available and do not significantly affect the properties of prilled bisphenol A.

DETAILED DESCRIPTION OF THE PREFERRED EMBODIMENTS

This invention is described with reference to the accompanying examples. The part and % are by weight.

EXAMPLE 1

Bisphenol A (purity 99,935%) was mixed with 1,000 ppm of 2,6-naphthalenedicarboxylic acid dimethyl ester (purity 99.9%, m.p. 190° C.) and melted by heating at 170° C. It was confirmed that the addition or nonaddition of the ester made no difference in the change of the melt color with time.

Bisphenol A kept at 170° C. was dropped through a nozzle with a diameter of 0.5 mm and the drops were allowed to fall in countercurrent contact with a cooling gas to produce prills of bispheol A with an average particle diameter of approximately 2,400 μm. The prills were screened, 40 prills with a particle diameter of 2,000 to 2,360 μm and 40 prills with a particle diameter of 2,360 to 2,800 μm were sampled and measured for the load strength (g/prill) with the aid of a digital force gauge manufactured by Imada and also for the melt color (190° C., 5 hr) (APHA). The results are shown in Table 1.

EXAMPLE 2

Prilled bisphenol A was prepared as in Example 1 except adding 1,000 ppm 9,9-bis(4-hydroxyphenyl)fluorene (purity 90% or more, m.p. 224° C.). The results are shown in Table 1.

EXAMPLE 3

Prilled bisphenol A was prepared as in Example 1 except adding 1,000 ppm of phenol novolak resin (phenol content 1.2%, softening point 120° C.). The results are shown in Table 1.

Comparative Example 1

Prilled bisphenol A was prepared as in Example 1 without additives. The results are shown in Table 1.

Comparative Example 2

Prilled bisphenol A was prepared as in Example 1 except adding 1,000 ppm of triphenyl phosphate (m.p. 50° C.). The results are shown in Table 1.

Comparative Example 3

Prilled bisphenol A was prepared as in Example 1 except adding 1,000 ppm of hydroxycellulose. The results are shown in Table 1.

TABLE 1

| | Load strength (g/prill) | | |
|---|---|---|---|
| | 2,000–2,360 μm | 2,360–2,800 μm | Melt color |
| Example 1 | 288 | 255 | #8 |
| Example 2 | 184 | 160 | #9 |
| Example 3 | 198 | 164 | #8 |
| Comparative example 1 | 169 | 151 | #8 |
| Comparative example 2 | 146 | 126 | #15 |
| Comparative example 3 | — | — | #175 |

EXAMPLE 4

A 12:1 mixture by mol of phenol and acetone was fed to a reactor packed with sulfonic acid type ion exchange resin at 80° C. and an SV of 0.8/hr. The reaction mixture was evaporated under reduced pressure to remove low-boiling compounds such as water and acetone and then cooled to 50° C. to crystallize out the adduct of bisphenol A and phenol.

The crystals were separated by filtration to yield the primary crystals and the primary mother liquor (reaction mother liquor). The primary mother liquor contained 8.0% of bisphenol A, 1.9% of bisphenol A isomers, and 1.9% of cyclic dimer (cyclic dimer of isopropenylphenol) and showed an acid content of 0.1 meq/l. The primary crystals were dissolved in commercial phenol until the concentration of bisphenol A became 25%, and the solution was heated to 80° C. and then cooled to 50° C. to crystallize out the adduct of bisphenol A and phenol. The crystals were separated by filtration to yield the secondary crystals and the secondary mother liquor (crystallization mother liquor). The secondary mother liquor contained 8.0% of bisphenol A, 0.2% of bisphenol A isomers, and 0.1% of cyclic dimer and its acid content was below the detection limit.

The secondary mother liquor (37.5 parts) was mixed with 1,000 parts of commerical bisphenol A, the mixture was placed in a vacuum evaporator at 170° C. and 0.3 Torr to remove phenol and then dropped through a nozzle with a diameter of 0.5 mm, and the drops formed are allowed to fall in countercurrent contact with a cooling gas to yield prills of bisphenol A with an average particle diameter of approximately 2, 000 μm.

The prills were screened, 40 prills with a particle diameter of 2,000 μm were sampled and measured for the load strength (g/prill) with the aid of a digital force gauge manufactured by Imada and also for the purity of bispheol A and the melt color (170° C., 2 hr) (APHA). The results are shown in Table 2.

EXAMPLE 5

Prilled bisphenol A was prepared as in Example 4 except using 3.8 parts of the primary mother liquor and 33.7 parts of phenol as additive. The results are shown in Table 2.

Comparative Example 4

Prilled bisphenol A was prepared as in Example 4 except using 37.5 parts of phenol as additive. The results are shown in Table 2.

TABLE 2

| | Composition of prills (wt. ppm) | | | | Load | Melt |
|---|---|---|---|---|---|---|
| | BPA | PhOH | Isomers | CD | strength | color |
| Example 4 | 999,185 | 95 | 115 | 40 | 124 | #20 |
| Example 5 | 999,215 | 90 | 112 | 45 | 121 | #35 |
| Comparative example 4 | 999,545 | 41 | 5 | 5 | 108 | #15 |

(Notes)
BPA: Bisphenol A
PhOH: Phenol
Isomers: Bisphenol A isomers
CD: cyclic dimer

What is claimed is:

1. In granulation of molten bisphenol A, a process for preparing prilled bisphenol A which comprises:

adding one kind or two or more kinds of compounds soluble in molten bisphenol A, not adversely affecting the melt color of bisphenol A to any extent and having a melting point of 60° C. or more, to bisphenol A wherein said compounds are selected from the group of aromatic dicarboxylic acid diesters, phenolic compounds having two phenolic hydroxyl groups (excepting bisphenol A), hydrogenation products of phenolic compounds having two phenolic hydroxyl groups, and phenolic resins; and granulating.

2. In granulation of molten bisphenol A, a process for preparing prilled bisphenol A which comprises:

adding one kind or two or more kinds of compounds soluble in molten bisphenol A, not adversely affecting the melt color of bisphenol A to any extent and having a melting point of 60° C. or more, to bisphenol A wherein said compounds are selected from the group of 2,6-naphthalenedicarboxylic acid dimethyl ester, 9,9-bis(4hydroxyphenyl)fluorene, and phenol novolak resins; and granulating.

3. A process for preparing prilled bisphenol A as described in claim 1 or claim 2 wherein the amount of said compounds to be added to bisphenol A is 100 to 2,000 ppm based on bisphenol A.

4. In granulation of molten bisphenol A, a process for preparing prilled bisphenol A which comprises adding the reaction mother liquor or crystallization mother liquor produced in the manufacturing step of bisphenol A to bisphenol A or the adduct of bisphenol A and phenol or a mixture of bisphenol A and phenol, removing the phenol, and granulating.

5. A process for preparing prilled bisphenol A as described in claim 4 wherein said reaction mother liquor or crystallization mother liquor is added to bisphenol A in a proportion of 100 to 2,000 ppm as increment of trace impurities in bisphenol A.

6. A process for preparing prilled bisphenol A as recited in claim 1 or claim 2 wherein the purity of bisphenol A in which said compounds are added is more than 99.9% and the amount of said compounds to be added to bisphenol A is 100 to 2,000 ppm based on bisphenol A.

* * * * *

UNITED STATES PATENT AND TRADEMARK OFFICE
CERTIFICATE OF CORRECTION

PATENT NO. : 5,371,302
DATED      : December 6, 1994
INVENTOR(S): Yanai et al

It is certified that error appears in the above-indentified patent and that said Letters Patent is hereby corrected as shown below:

On the title page, item [75], change "Tsohikazu" to --Toshikazu--.

Signed and Sealed this

Twenty-first Day of March, 1995

Attest:

BRUCE LEHMAN

*Attesting Officer*         *Commissioner of Patents and Trademarks*